United States Patent
Chow et al.

(10) Patent No.: US 6,491,900 B2
(45) Date of Patent: Dec. 10, 2002

(54) ANTI-CARIOUS CANDIES AND CONFECTIONS

(75) Inventors: Laurence C. Chow, Potomac, MD (US); Shozo Takagi, Gaithersburg, MD (US); Gerald L. Vogel, Germantown, MD (US)

(73) Assignee: American Dental Association Health Foundation, Gaithersburg, MD (US)

( * ) Notice: Subject to any disclaimer, the term of this patent is extended or adjusted under 35 U.S.C. 154(b) by 0 days.

(21) Appl. No.: 09/771,473

(22) Filed: Jan. 26, 2001

(65) Prior Publication Data

US 2001/0033831 A1 Oct. 25, 2001

Related U.S. Application Data

(60) Continuation-in-part of application No. 09/535,642, filed on Mar. 24, 2000, now abandoned, which is a division of application No. 09/089,286, filed on Jun. 2, 1998, now abandoned, which is a division of application No. 08/704,420, filed on Aug. 20, 1996, now Pat. No. 5,833,954.

(51) Int. Cl.[7] .................. A61K 7/16; A23K 1/16; A23K 1/304; A23G 3/00
(52) U.S. Cl. ............... 424/57; 424/435; 424/440; 426/658; 426/660; 426/74; 426/103
(58) Field of Search .................... 424/435, 440, 424/49–58; 426/658, 660, 74, 103

(56) References Cited

U.S. PATENT DOCUMENTS

| | | | | |
|---|---|---|---|---|
| 4,405,600 A | * | 9/1983 | Besic | 424/57 |
| 4,515,770 A | * | 5/1985 | Besic | 424/57 |
| 5,182,114 A | * | 1/1993 | Blaser et al. | 424/673 |
| 5,603,922 A | * | 2/1997 | Winston et al. | 424/57 |
| 5,607,716 A | * | 3/1997 | Doherty et al. | 426/660 |
| 5,645,853 A | * | 7/1997 | Winston et al. | 424/440 |
| 5,817,296 A | * | 10/1998 | Winston et al. | 424/57 |
| 5,833,954 A | * | 11/1998 | Chow et al. | 424/439 |
| 5,833,957 A | * | 11/1998 | Winston et al. | 424/57 |
| 5,958,380 A | * | 9/1999 | Winston et al. | 424/57 |
| 5,993,786 A | * | 11/1999 | Chow et al. | 424/49 |
| 6,036,944 A | * | 3/2000 | Winston et al. | 424/57 |

FOREIGN PATENT DOCUMENTS

EP      885 568      * 12/1998

* cited by examiner

*Primary Examiner*—Shep K. Rose
(74) *Attorney, Agent, or Firm*—Banner & Witcoff, Ltd.

(57) ABSTRACT

Candies and confectioneries containing non-toxic sparingly soluble calcium and phosphate compounds as additives, cause the release of calcium and phosphate ions into the oral cavity gradually and persistently for a period no less than five minutes. Released calcium phosphate ions diffuse into partially demineralized tooth enamel or dentin, leasing to remineralization and repair of caries lesions, dental plaque, open dentinal tubules and exposed dentin. Agents and methods for remineralization of teeth, for reducing or eradicating cariogenic challenge in plaque following sucrose intake for producing effective anticaries actions without the use of fluoride and for desensitizing hypersensitive teeth are disclosed.

20 Claims, 3 Drawing Sheets

ANTI-CARIOUS CANDIES AND CONFECTIONS

CROSS REFERENCE TO RELATED APPLICATIONS

This application is a continuation-in-part application of a continuation application Ser. No. 09/535,642 filed Mar. 24, 2000 now abandoned which is a division application of U.S. Ser. No. 09/089,286 filed Jun. 2, 1998 now abandoned which is a division of U.S. Ser. No. 08/704,420 filed Aug. 20, 1996, now U.S. Pat. No. 5,833,954 which is incorporated herewith by reference and related U.S. Pat. No. 5,993,786, also incorporated herewith by reference.

This invention was made, in part, during research activities that were supported in part by Grants DE05354 and DE10840 from the NIDR to the ADAHF and carried out at the National Institute of Standards and Technology. The Government may have certain rights in the invention.

BACKGROUND OF THE INVENTION

1. Field of the Invention

This invention comprises the use of non-toxic sparingly soluble calcium and phosphate compounds as additives, particularly to candies and confectioneries that cause the release of calcium and phosphate ions into the oral cavity gradually and persistently for an appropriate and therapeutically useful period. The released calcium phosphate ions can diffuse into partially demineralized tooth enamel or dentin, leading to remineralization and repair of the caries lesion. The released calcium phosphate ions can also diffuse into dental plaque to cause remineralization of teeth and to reduce or eradicate cariogenic challenge in plaque following sucrose or sugar intake. Thus, these formulations can produce effective anticaries actions without the use of fluoride. The released calcium phosphate ions can also cause precipitation of calcium phosphate minerals inside open dentinal tubules and on exposed dentine surfaces to desensitize hypersensitive teeth. These agents will have minimal adverse effects and require little effort on the part of the user.

2. Summary of the Related Art

Edibles, chewables and confections have the potential of being an effective vehicle for delivering therapeutic agents to teeth because they permit protracted contact of the agent to the teeth with minimal effort on the part of a patient. Despite the desirability of such items as a vehicle for delivering anticarious agents to teeth, no effective embodiments of anticarious confections or candies (with or without sugar) have been developed in the art.

The effectiveness of prior attempts at using potential anticarious agents in edibles for oral consumption, i.e., chewing gums, for example, was reviewed by Edgar and Geddes (1990, Br. Dent. J. 24: 173–176). For example, dicalcium phosphate dihydrate (DCPD; $CaHO_4.2H_2O$), was used at a dose of 7.5 wt % and assessed for its effects on the calcium (Ca) and phosphate ($PO_4$) concentrations in saliva (Pickel and Bilotti, 1965, J. Alabama Med. Soc. 2: 286–287). A chewing gum containing 10 wt % DCPD was assessed for anticarious effects in two different clinical studies (Finn and Jamison, 1967, J. Amer. Dent. Assoc. 74: 987–995; Richardson et al., 1972, J. Canad. Dent. Assoc. 6: 213–218). The results from the Richardson study showed that, although sugar-DCPD gum produced a lower caries score than did the gum containing sugar alone, the cariogenicity of the sugar-DCPD gum was equivalent to that of sugar-free gum. The marginal degree of effectiveness of DCPD as an anticaries gum additive in this study was accepted in the art as demonstrating that DCPD was ineffective as an anticarious agent. As a result of this study, there has been little interest or activity in the art in using calcium phosphate-containing gums as anticarious agents.

The feasibility of using two new calcium phosphate additives in bubble gum has been evaluated for effectiveness in increasing salivary mineral saturation levels and/or enhancing salivation (Chow et al., 1994, J. Dent. Res. 73: 26–32). In these in vivo studies, monocalcium phosphate monohydrate (MCPM; $Ca(H_2PO_4)_2.H_2O$) and an equimolar mixture of dicalcium phosphate anhydrous (DCPA; $CaHPO_4$) and tetracalcium phosphate (TTCP; $Ca_4(PO_4)_2O$) were used as chewing gum additives. These studies showed that both the MCPM and DCPA/TTCP gums increased the calcium and phosphate concentrations in saliva during a chewing period of 16 minutes. The extent of increase was much greater than those produced by gums containing DCPD. The degree of saturation with respect to tooth mineral was significantly increased by both experimental gums, with greater increase being produced by the DCPA/TTCP gum. U.S. Pat. Nos. 5,037,639; 5,268,167; 5,427,768; and 5,437,857; issued to Tung, disclose and claim the use of amorphous calcium phosphate ($Ca_3(PO_4)_2$) and derivatives as chewing gum additives for tooth remineralization.

While some of the above additives have had efficacy under some conditions, shortcomings have been associated with each. The DCPA/TTCP mixture requires an extensive preparation process: TTCP must be prepared in a furnace at a high temperature (1500° C.) and then blended with commercially-available DCPA after each calcium phosphate salt has been ground to the desired particle size. ACP compounds must be precipitated in aqueous systems, thereby having variable composition and relatively undefined particles size. Also, the stability of ACP in gum base or a gel and perhaps in a confection may be limited, and a stabilizer may be required to achieve the desired shelf life.

Other calcium-containing compounds have been studied for their effectiveness in remineralization of teeth in situ. U.S. Pat. No. 5,378,131 to Greenberg disclosed the use of calcium glycerophosphate as a chewing gum additive for dental health benefits. This patent also disclosed the use of several other calcium compounds, including calcium lactate and calcium gluconate, to achieve an anticaries effect when used as a chewing gum additive. However, chewing gums containing calcium compounds as additives can only raise calcium concentration levels in saliva. In fact, phosphate concentration levels would be expected to be decreased as a result of chewing calcium-containing gums, based on the showing that saliva phosphate levels decrease with increased salivation stimulated by gum chewing (Chow et al., ibid.). Thus, these calcium-containing chewing gums disclosed by Greenberg are cariostatic, rather than anticarious. Consequently, there is a need for vehicles that release phosphate ions into the oral cavity in conjunction with increased calcium ion concentration to provide an anticaries effect not found in edibles known in the prior art.

In contrast to the recognized likely desirability of chewing gum as a vehicle for delivery of anticarious agents, candies have not been generally recognized as a means for delivering calcium and phosphate ions into the oral environment. A major reason for this is that sugar, the major ingredient of candies, is the chief culprit of dental caries. With the advent of sugar-free candies (i.e., candies that do not contain significant amount of fermentable carbohydrates), however, candies can be an effective means of delivering therapeutic agents for dental caries.

SUMMARY OF THE INVENTION

This invention provides candies and confectioneries (both sugar based and sugarless) that are formulated to release calcium and phosphate ions into the mouth of a human patient.

The invention provides a calcium phosphate-containing composition comprising a candy or confectionery and further comprising a calcium phosphate salt. In preferred embodiments, the candy or confectionary is sugar-free, though sugar-based candy may provide the benefits of the invention. In a most preferred embodiment, the calcium phosphate salt is α-tricalcium phosphate. In other preferred embodiments, the calcium phosphate salt is β-tricalcium phosphate, monocalcium phosphate monobasic, dicalcium phosphate anhydrous, dicalcium phosphate dihydrate, octacalcium phosphate, tetracalcium phosphate, and mixtures and combinations thereof. Preferably, the calcium phosphate salt comprises from about 0.5 to about 10 percent of the candy formulation by weight (weight percent, or wt %). More preferably, the calcium phosphate salt comprises from about 1 to about 5 wt % of the candy formulation. In the sugar-free candies of the invention, the calcium phosphate salts are provided with a particle size of less than about 50 μm, and more preferably having a particle size of from about 1 to about 20 μm. Sparingly-soluble calcium phosphate salts are appropriate but are not required for this embodiment of the invention, due to the preferred composition of the candies and confectioneries of the invention as described in detail herein. Although sugar-free candies and confectioneries are preferred, calcium phosphate-containing embodiments of the candies and confectioneries of the invention prepared using sugar (e.g., sucrose) are within the scope of the invention. In such embodiments, it will be recognized that the cariostatic and remineralizing benefits of the calcium phosphate components of the inventive candies and confectioneries will outweigh the cariogenic propensity of sugar.

In a further aspect, the invention provides a calcium phosphate-containing candy or confectionery that comprises a calcium compound and a phosphate salt. In preferred embodiments, the candy or confectionery is sugar-free. In preferred embodiments, the calcium compound is a sparingly-soluble calcium salt of glycerophosphate, lactate, gluconate, or fumarate. In other preferred embodiments, the calcium compound is a soluble compound, and is preferably calcium acetate or calcium chloride. In these embodiments, the candy is formulated to slow the release of calcium ions from the soluble calcium compound so that calcium ions are released over a 5 to 15 minute period.

Preferably, the candies provided in this aspect of the invention are formulated to contain calcium compounds at from about 0.5 to 10 weight percent of the candy. More preferably, the calcium compounds comprise from about 1 to about 5 weight percent of these candies. Additionally, the calcium compounds provided in the candies of this aspect of the invention are provided having a particle size of less than 50 μm, more preferably from about 1 to about 20 μm.

The candies of this aspect of the invention are also formulated to contain a phosphate salt. Preferred phosphate salts include but are not limited to $Na_2HPO_4$, $NaH_2PO_4$, and $Ca(H_2PO_4)_2 \cdot H_2O$. Preferably, the candies in this aspect of the invention are formulated to contain phosphate salts at from about 0.5 to 10 weight percent. More preferably, the phosphate salts comprise from about 1 to about 5 weight percent of these candies. Additionally, the phosphate salts provided in the candies of this aspect of the invention are provided having a particle size of less than 50 μm, more preferably from about 1 to about 20 μm.

Although sugar-free candies and confectioneries are preferred, calcium phosphate-containing embodiments of the candies and confectioneries of the invention prepared using sugar (e.g., sucrose) are within the scope of this aspect of the invention.

The invention also provides methods for remineralizing teeth to reduce or eliminate dental caries and other dental disease. The methods of the invention are provided wherein a human patient simply ingests into the oral cavity the candies or confectioneries to release calcium and phosphate ions into the mouth and onto teeth. In a preferred embodiment, the candy or confectionery is used as a lozenge, from about one to about five minutes, more preferably from about three to about ten minutes, and most preferably from about five to about fifteen or twenty minutes, to effect the release of calcium and phosphate ions into the mouth and in contact with teeth.

A preferred use for the methods of this invention is for remineralizing a dental lesion in a human. Another preferred use for the methods of the invention is for remineralizing dental plaque in a human. Yet another preferred use for the methods of this invention is for reducing cariogenic challenge to human teeth. The methods of the invention are also preferably used for desensitizing hypersensitive human teeth, and for remineralizing open dentinal tubules and exposed dentine surfaces in human teeth.

Certain preferred embodiments of the candies and confectioneries as well as useful methods for using such embodiments for treating and remineralizing teeth, are described in greater detail in the following sections of this application.

BRIEF DESCRIPTION OF THE DRAWING

In the detailed description which follows, reference will be made to the drawing comprised of the following figures.

DETAILED DESCRIPTION OF THE INVENTION

Figure 1:
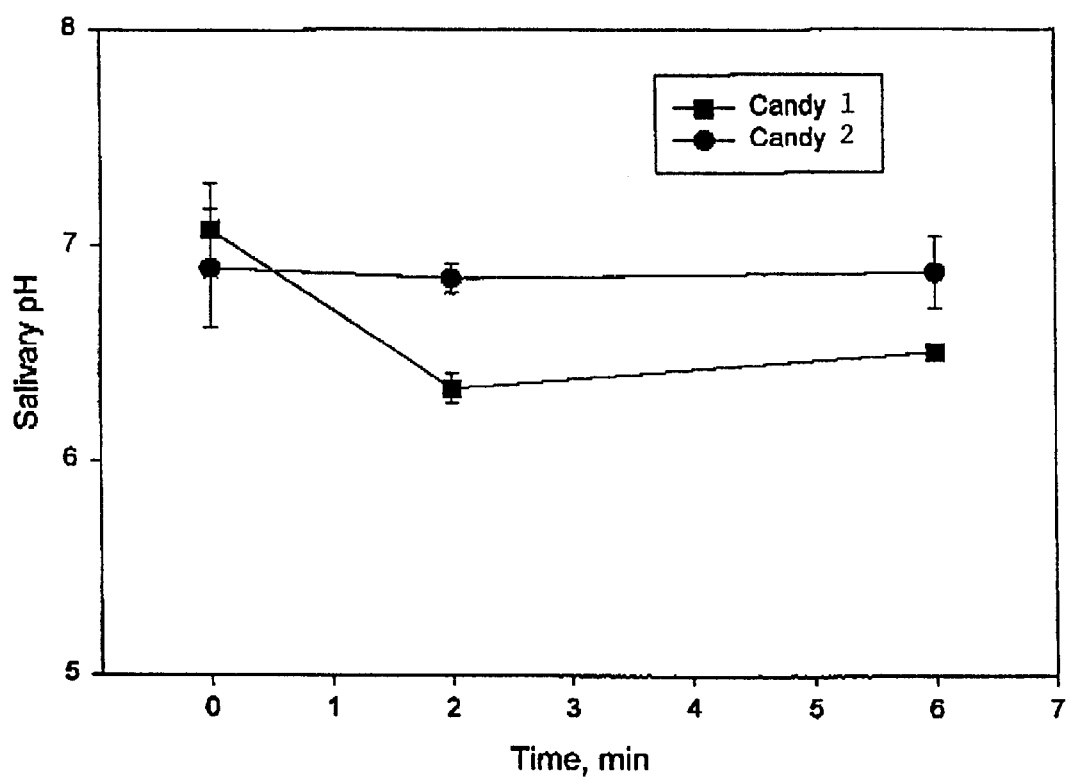
FIG. 1 is a graph setting forth the recorded pH of saliva during the time period of the tests performed to determine the effective release of calcium and phosphate ions in the oral cavity from a sugar based confection.

It has been known for some time that hydroxyapatite materials have the basic properties of human bones and teeth. A considerable amount of research has been directed to the remineralization of incipient dental lesions, including plaque deposits, by deposition of hydroxyapatite, $Ca_5(PO_4)_3OH$, on such lesions, so that the hydroxyapatite is incorporated into the dental structure at the point of lesion.

Remineralization of tooth enamel has been carried out experimentally both in vivo and in vitro. These studies have concentrated on the remineralizing properties of saliva and synthetic solutions supersaturated with respect to hydroxyapatite. Candies and confectioneries, as provided herein are useful as vehicles for delivering hydroxyapatite-depositing calcium phosphate compositions to teeth in vivo. An advantage of these delivery vehicles is that calcium phosphates and compounds that release calcium and phosphate ions into the mouth are provide as simple mixtures in the candy or confectionery because delivery to teeth is effectively achieved simply by having a human use the delivery vehicle of the invention (e.g., by ingesting the candies and/or confectioneries).

Compounds that release calcium and phosphate ions are selected from a number of commercially-available and other compounds that are recognized as food additives in other contexts. All such additives encompassed by the present invention are intended to be non-toxic. For the purpose of this invention, the term "non-toxic" is intended to conform with accepted and established definitions of safety, such as are described by the designation "generally accepted as safe" by the Food and Drug Administration. Also encompassed in this definition are those compounds that have been added to food for some time and which are recognized as safe under conditions of their intended use. The additives of the invention, including calcium and phosphate salts should be non-toxic enough for oral use at the intended levels on a regular basis, and stable for the desired shelf life.

Preferred calcium ion-releasing compounds are sparingly soluble calcium-containing salts of biologically-compatible acids and other basic calcium compounds, i.e., calcium compounds having a solubility greater than about 0.1% and less than about 10% under conditions of neutral pH. Sparingly soluble calcium compounds include, but are not limited to, the calcium salts of gluconate, glycerophosphate, lactate, and fumarate, $Ca(OH)_2$, CaO monocalcium phosphate, dicalcium phosphate anhydrous, dicalcium phosphate dihydrate, α-tricalcium phosphate, octacalcium phosphate, tetracalcium phosphate, and combinations and mixtures thereof.

In order to obtain significant calcium ion release, the calcium source should have a solubility that is greater than 0.5% at neutral pH; solubilities of 2% and above are preferred. Preferred calcium salts are sparingly soluble, that is, having a solubility of less than 10% at neutral pH. Calcium carbonate and calcium citrate and calcium tartrate (the calcium salts of two commonly-used food acids) are believed, too, to be insoluble to produce effective release. On the other hand, highly soluble calcium-containing compounds such as calcium acetate and calcium chloride are useful in or with candies and confectioneries because they generally take five minutes or longer to dissolve.

The anticaries effects of calcium ion-releasing compounds of the invention are significantly augmented by adding a non-toxic phosphate salt as a second additive. Preferred phosphate salts include sodium phosphate (most preferably comprising an equimolar mixture of $Na_2HPO_4$ and $NaH_2PO_4$, to maintain pH at 7). Addition of sodium phosphate to the calcium ion-releasing additives of the invention results in the desired release of both calcium and phosphate ions in quantities capable of depositing calcium phosphate mineral (including hydroxyapatite) on the surface of teeth in vivo. In alternative embodiments, a sparingly-soluble calcium source can be admixed with a calcium phosphate salt, such as MCPM, which serves as a source for both calcium and phosphate ions.

Candies and confectioneries of the invention comprise preferably non-sugar sweeteners such as sorbitol, mannitol, aspartame and saccharine. Sugar (specifically sucrose, fructose, glucose, and combinations thereof) containing candies and confectioneries are also provided by the invention. Flavorings, such as citrus and other flavorings, that are naturally acidic are used to provide an optional, but advantageous acidic environment. In addition, calcium compounds having substantially higher solubility than those calcium compounds useful in gums and dentifrices can be used in the candies and confectioneries as provided herein; non-limiting examples of such calcium compounds are calcium chloride and calcium acetate. Preferred candies of the invention are non-chewable hard candies which dissolve over time in saliva. Preferably, particles of the calcium and phosphate compounds comprising the candies and confectioneries of the invention are uniformly or homogeneously distributed throughout the candy or confectionery. In preferred embodiments, the candies and confectioneries of the invention are formulated wherein calcium and phosphate ions are released from the candies and confectioneries as they dissolve and remain active because they are embedded in the candy and thus not subject to dehydration by exposure to water (e.g., ambient moisture). It will be understood that the release rate of the calcium and phosphate ions depends on the concentration and distribution of these ions in the candies and confectioneries and on the rate of dissolution of the candies and confectioneries, which, in turn, is dependent on the surface area of the candy or confectionery and its composition. In these formulations, the solubilities of the calcium and phosphate-containing compounds contribute relatively less to the release rates of calcium and phosphate ions than does the candy or confectionery dissolution rate. Calcium and phosphate ion release kinetics can be formulated accordingly by those of skill in the art based on these parameters.

An additive of particular significance in dental applications is fluoride containing compounds. In embodiments of this invention, fluoride salts such as NaF, $CaF_2$, $SnF_2$, $Na_2PO_3F$ or $Na_2SiF_6$ are optionally added in sufficient quantity they increase the rate of formation of HA and fluorapatite. Preferably, embodiments of the invention will have a fluoride content of about 200 to 2200 ppm.

The following Examples are intended to further illustrate certain preferred embodiments of the invention and are not limiting in nature.

EXAMPLES

Preparation of Calcium Phosphate-containing Candies

Both sugar-free candies (Table I) and sugar-containing candies (Tables II and III) are described. In this aspect of the invention, calcium and phosphate sources can be combined in the same phase without concern of premature hydroxyapatite-producing reactions between the two compounds since there is essentially no free water in such candies. That is, the candy serves as an anhydrous medium or matrix for the particles of calcium and/or phosphate salts and insulates the active materials until ingested into the oral cavity and exposed to saliva. Particle size and distribution of active ingredients is as referenced previously.

TABLE I

Remineralizing Sugar-Free Candy Example

| COMPONENT | AMOUNT |
| --- | --- |
| Calcium glycerophosphate | 8.4 g |
| Sodium monohydrogen phosphate heptahydrate | 5.36 g |
| Sodium dihydrogen phosphate dihydrate | 3.12 g |
| Sorbitol, flavoring, coloring | q.s. to 100 g |

TABLE II

Remineralizing Candy Example

| COMPONENT | AMOUNT |
|---|---|
| α-tricalcium phosphate | 8 g |
| Sugar, corn syrup, flavoring, coloring | q.2. to 100 g |

Following is a further example of testing of candy compositions for the release of calcium and phosphate ions into the oral cavity.

Sample Preparation

A sugar based candy composition of a type known to those of ordinary skill in the art and which includes the following inactive ingredients was prepared: sugar, corn syrup, flavoring and food color. The sugar and corn syrup constituted approximately at least 95% of the weight percent of the candy. These materials constituted the inactive ingredients. The active ingredients for the two tests that were performed are set forth in the following table:

TABLE III

Composition of Test Candies

| ACTIVE INDREDIENT | Wt % CANDY NO. 1 | Wt % CANDY NO. 2 |
|---|---|---|
| Calcium lactate | 3.1 | 0.62 |
| Sodium phosphate, Monobasic | 0.7 | 0.14 |
| Sodium phosphate, dibasic | 1.0 | 0.20 |

Inactive ingredients include sugar, corn syrup, flavoring, and food color.

The inactive ingredients were prepared and heated and were thus in a liquidous or flowable state. The active ingredients were then added, the active ingredients having particle sizes in the range set forth previously. Each sample was then mixed so that there was a uniform dispersion of the active ingredients. Samples comprising approximately 4 grams per sample were prepared for further testing by human ingestion.

Test For Release of Calcium and Phosphate Ions

The following test protocol was followed and demonstrated a significant release of calcium and phosphate ions in the oral cavity:

Subjects

Three subjects, shown to have a non-stimulated salivary flow rate of greater than 0.2 mL per minute, were recruited.

Protocol

Subjects used a test candy at time=0 minute. Each subject was asked to expectorate into a pre=weighed tube. Saliva samples were collected for a two minute interval three times, −2 to 0 minutes, 0 to 2 minutes, and 4 to 6 minutes. The −2 to 2 minutes sample served as a baseline control.

Sample Analysis

Immediately after collection, the saliva sample was placed under a 5% $CO_2$–95% $N_2$ atmosphere and the pH and free calcium concentration/activity were measured with a Ca-ion specific electrode/combination pH electrode pair. About 500 μL of the saliva sample was then transferred into a centrifuge tube and centrifuged. The clarified saliva was immediately filtered through a 0.2 μm filter and 25 μL of 1 mol/L $HClO_4$ was added to prevent precipitation of mineral ions. This sample was then analyzed for total calcium and phosphate content by spectrophotometric methods (Vogel et al., *J Dent Res* 77:518–524, 1998).

The test results are set forth in the following table and are graphically represented in attached FIGS. 1, 2 and 3.

TABLE IV

Salivary Composition as a Function of Time While Consuming Test Candies

| CANDY NO. | TIME MINUTES | PH | Free [Ca], mmol/L | [P] mmol/L |
|---|---|---|---|---|
| 1 | −2 to 0[1] | 7.07 ± 0.22[2] | 1.46 ± 0.27 | 7.68 ± 2.40 |
| 1 | 0 to 2 | 6.34 ± 0.07 | 6.48 ± 0.78 | 9.50 ± 0.93 |
| 1 | 4 to 6 | 6.51 ± 0.02 | 5.05 ± 0.83 | 8.85 ± 2.62 |
| 2 | −2 to 0 | 6.90 ± 0.28 | 1.50 ± 0.52 | 6.65 ± 1.73 |
| 2 | 0 to 2 | 6.85 ± 0.07 | 3.20 ± 0.31 | 5.91 ± 0.42 |
| 2 | 4 to 6 | 6.88 ± 0.17 | 3.88 ± 0.60 | 4.54 ± 1.04 |

[1]Candy use started at time = 0 minutes. The −2 to 0 minute sample was collected before candy use and served as a baseline control.
[2]Mean ± std. Dev. (n = 3).

As a result of these test results, the following conclusions were drawn. Both of the candy samples produced a significant increase in salivary calcium levels during use. Typically the candies would dissolve in the oral cavity at least 85% by weight in approximately six minutes. The dissolution was believed to be uniform with time. The ion release was effected as a result of the aqueous interaction of saliva with the active ingredients. That is, the active ingredients were generally homogeneously distributed in the matrix of the candy. As the candy would dissolve, the active ingredients are released and come into contact with saliva thereby causing ion release as indicated by the experimental results. Note that the candy 1 contained greater amounts of calcium and phosphate additives and produced a greater calcium increase. Also to be noted is the rate of saliva increased 2–3 times during use of the candy thus indicating that the candy is an appropriate matrix or medium to deliver the additives in an ionic form. The salivary phosphate level is known to be significantly lower in stimulated saliva. This is believed to be the reason that the phosphate level was increased by candy no. 1, but not necessarily by candy no. 2 in the experimental results.

Figure 2:
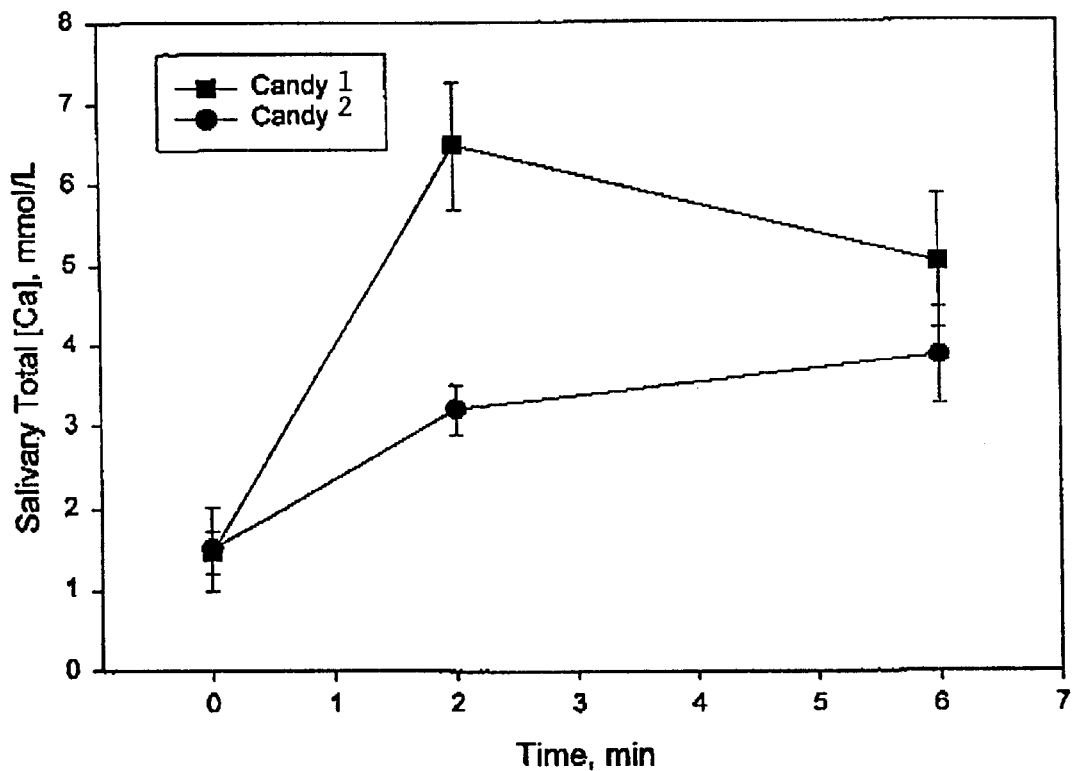
FIG. 2 is a graph setting forth the recorded quantitative release of calcium ions from a sugar based confection during the test time period in an oral cavity.
Figure 3:
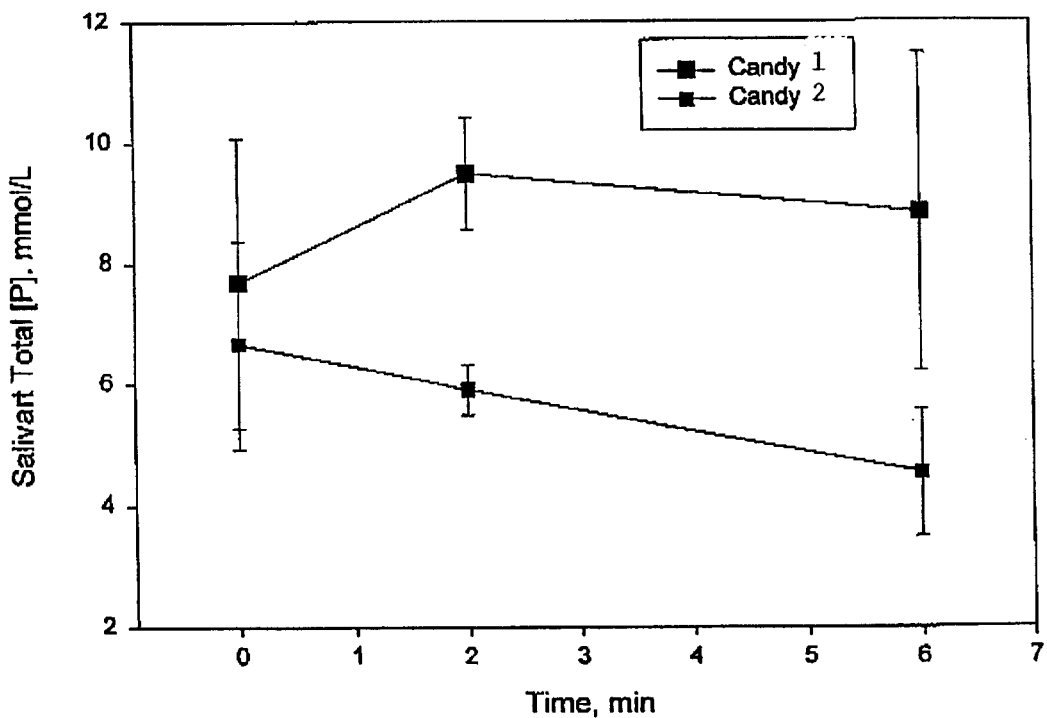
FIG. 3 is a graph setting forth the recorded quantitative release of phosphate ions from a sugar based confection during the test time period in an oral cavity.

FIGS. 1, 2 and 3 represent the experimental results reported in Table IV. The release of the ionic constituents was thus clearly effected by virtue of the interaction with the saliva, that interaction being the result of the fact that the candy precluded access of water to the active compounds until the active compounds were appropriately released from the candy matrix. The experimental results applied in the present experiments with respect to sugar based candies are also applicable with respect to non sugar based candies. The presence of the ionic materials in the saliva and in the oral cavity as so released will thus effect the appropriate and described beneficial result to protect the tooth enamels.

It should be understood that the foregoing disclosure emphasizes certain specific embodiments of the invention and that all modifications or alternatives equivalent thereto are within the spirit and scope of the invention as set forth herein.

What is claimed is:

1. A confectionery system for remineralization of teeth consisting essentially of:
   a confection comprised of an inactive material selected from the group consisting of edible sugars essentially free of water and edible sugar free compounds mixed with edible sugars essentially free of water;
   a calcium compound in particle form having a particle size less than about 50 μm; and
   a separate phosphate salt in particle form having a particle size less than about 20 μm, both the compound and the salt mixed in the confection without the presence of ambient water and without chemical reaction therebetween, said compound and said salt capable, respectively, of sustained release of calcium and phosphorous ions in the presence of water, thereby forming hydroxyapatite as an end product on a surface when said confection is consumed in an oral cavity and the compound particles and salt particles are simultaneously exposed to saliva.

2. A confection according to claim 1 wherein the confection is sugar free.

3. A confection according to claim 1 wherein the calcium compound is selected from the group consisting of calcium acetate and calcium chloride.

4. A confectionery according to claim 1 wherein the calcium compound is a sparingly-soluble calcium compound.

5. A system according to claim 1 wherein the sparingly-soluble calcium compound is selected from the group consisting of the calcium solution glycerophosphate, lactate, glgconate and fumarate.

6. A system according to claim 1 wherein the calcium compound comprises from 0.5 to 10 weight of the confection.

7. A system of claim 1 wherein the calcium compound comprises from 1 to 5 weight percent of the confection.

8. The confection of claim 1 wherein the calcium compound comprising the candy or confectionery has a particle size of less than 50 $\mu$m.

9. A system of claim 1 wherein the phosphate salt is selected from the group consisting of $Na_2HPO_4$, $NaH_2PO_4$, and $Ca(H_2PO_4)_2$—$H_2O$.

10. A system of claim 1 wherein the phosphate salt comprises 0.5 to 10 weight percent of the confection.

11. The confection of claim 1 wherein the phosphate salt comprising the confection has a particle size of 1 to 20 $\mu$m.

12. The confection of claim 1 wherein the phosphate salt comprising the confection has a particle size of 1 to 20 $\mu$m.

13. A method of remineralizing a dental lesion in a human, the method comprising the step of having the human orally consume a sugar free confectionery according to claim 1.

14. A method of remineralizing a dental lesion in a human, the method comprising the step of having the human orally consume a confectionery system according to claim 1.

15. A method of reducing carciogenic challenge to human teeth, the method comprising the step of having the human orally consume a confectionery system according to claim 1.

16. A method of desensitizing hypersensitive human teeth, the method comprising the step of having the human orally consume a confectionery according to claim 1.

17. A calcium phosphate containing confection comprising, in combination:

a confection mixture comprising a water soluble sugar selected from the group consisting of sucrose, fructose, glucose and mixtures thereof; and a calcium phosphate salt selected from the group consisting of α-tricalcium phosphate, β-tricalcium phosphate, tetracalcium phosphate, monocalcium phosphate monobasic, dicalcium phosphate anhydrous, dicalcium phosphate dihydrate, octacalcium phosphate and mixtures, entrained within the confection.

18. A calcium phosphate containing confection comprising, in combination:

a confection mixture comprising an edible, water soluble, sugar free compound; and a calcium phosphate salt selected from the group consisting of α-tricalcium phosphate, β-tricalcium phosphate, tetracalcium phosphate, monocalcium phosphate monobasic, dicalcium phosphate anhydrous, dicalcium phosphate dihydrate, octacalcium phosphate and mixtures, entrained within the confection.

19. A confection composition consisting essentially of:

an inactive material selected from the group consisting of edible sugars, edible sugar free compounds and mixtures thereof;

a calcium compound in particle form, said calcium compound particles having a size less than about 50 $\mu$m; and a phosphate salt in particle form wherein the said phosphate salt particles have a size less than about 20 $\mu$m, and wherein the calcium compound is selected from the group consisting of calcium acetate, calcium chloride, calcium salt of glycerophosphate, lactate, gluconate, fumarate, and mixtures thereof;

wherein the phosphate salt is selected form the group consisting of $Na_2HPO_4$, $NaH_2PO_4$, and $Ca(H_2PO_4)_2H_2O$ and further wherein the compound particles and salt particles are maintained in a non-aqueous condition in said confection composition.

20. A confectionary system for remineralization of teeth consisting essentially of:

a confection comprised of an inactive, edible, sucrose composition;

a calcium lactate salt compound in particle form wherein the salt compound particles have a size less than about 50 $\mu$m; and a sodium phosphate salt compound in particle form, wherein the phosphate salt compound particles have a size less than about 20 $\mu$m, both of said compounds in particle form mixed in the confection and maintained without the presence of water, said compounds capable in combination of sustained release of calcium and phosphorus ions when simultaneously in the presence of saliva to form hydroxyapatite as an end product on a surface in the oral cavity.

* * * * *